US00PP10340P

United States Patent [19]

Sorensen

[11] Patent Number: Plant 10,340

[45] Date of Patent: Apr. 21, 1998

[54] OSTEOSPERMUM PLANT NAMED 'CAPE DAISY NAIROBI'

[75] Inventor: Carl Aksel Kragh Sorensen, Åbyhoj, Denmark

[73] Assignee: Paul Ecke Ranch, Encinitas, Calif.

[21] Appl. No.: 698,341

[22] Filed: Aug. 15, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV-ROM Plant Variety Database 'Cape Daisy Nairobi', PBR OTS0021, 1994.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Cape Daisy Nairobi', particularly characterized by its mounding growth habit with abundant white flower coloration, early flowering, dark green foliage and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Cape Daisy Nairobi', and was developed by the inventor Carl Aksel Kragh Sorensen in Aarhus, Denmark in 1975 by crossing the cultivar designated 'Cape Daisy Zimba' with the cultivar 'Nandi', an unpatented plant.

Asexual reproduction by terminal (stem tip) cuttings taken by me or under my supervision at Peterminde Greenhouse in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique pure white flower with a light blue back.
2. An upright compact growth habit.
3. Early flower response.
4. Well suited for 6" pots, nursery containers, and hanging baskets. 'Cape Daisy Nairobi' is similar to the unprotected cultivars 'Nandi' and 'Sunny Boy'. The growth habit of 'Cape Daisy Nairobi' is more compact, it flowers earlier, and has darker green foliage than either 'Nandi' or 'Sunny Boy'.

Chart A compares 'Cape Daisy Nairobi' with 'Cape Daisy Zimba' which is the closest plant to the knowledge of the inventor. 'Cape Daisy Zimba' is described and illustrated in co-pending U.S. patent application, Ser. No. 08/695,341.

CHART A

| Characteristic | 'Cape Daisy Zimba' | 'Cape Daisy Nairobi' |
|---|---|---|
| Plant Height (above the pot) | 32 cm | 28 cm |
| Plant Width | 66 cm | 50 cm |
| Flower Head Diameter | 7.5 cm | 7.7 cm |
| Inflorescence Color | White with yellow center | White with blue center |

DESCRIPTION OF THE PHOTOGRAPH

The accompanying colored photograph is a side perspective view of the new cultivar, showing color as true as it is reasonably possible to obtain in a colored reproduction of this type.

DESCRIPTION OF PLANT

The following is a detailed description of my new Osteospermum cultivar based on plants grown under commercial practice in Encinitas, Calif. One rooted cutting was transplanted into a 17 cm florist pot on Jan. 8, 1996. Plants were pinched on Jan. 29, 1996, and received plant growth regulator on February 12 and 26. The values, measurements and observations noted below were taken from plants in bloom on Apr. 15, 1996. Standard growth retardant applications for 'Cape Daisy Nairobi' included 1–2 applications of daminozide/butanedioic acid mono (2.2 dimethylhydrazide) at a rate of 2500 ppm. Applications were made as foliar sprays. Growth retarding chemicals generally reduced plant height by about ⅓.

On Apr. 21, 1996, I observed a plant in a 17 cm florist pot 13 cm tall. This pot had one branched plant with an overall height of 41 cm and an overall width of 50 cm. This plant had 6 strong branches, originating from the soil line. Each branch was approximately 26 to 34 cm long terminating in a flower. At observation, there were 9 flowers open and 79 flower buds in various stages of development. Four to six secondary shoots subtend the terminal flower from the top 4–6 nodes on the primary shoot. These secondary shoots also terminated in a flower.

Color references are made to The Royal Horticultural Society Colour Chart (R.H.S.), except where general terms of ordinary dictionary significance are used.

The Plant

Origin: Seedling from cross pollination.

Parentage: Cross between seed parent 'Cape Daisy Zimba' and pollen parent 'Nandi'.

Classification:

*Botanical.*—*Osteospermum ecklonis.*

*Common name.*—Osteospermum.

*Cultivar name.*—'Cape Daisy Nairobi'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

Plant description:

A. *Form.*—Symmetrical, mounded perennial shrub, with good branching characteristics after pinching, giving the plant in a full appearance.

B. *Habit of growth.*—Vigorous, mounding habit, producing approximately 20 leaves per stem and terminating in flowers. After the initial flower is formed, typically three subordinate axillary shoots develop from the nodes of uppermost leaves producing additional flowering shoots. This process is continuous so long as night temperatures remain below 16° C.

C. *Foliage description.*—1. Leaf shape: Oblanceolate with acute tip and attenuate leaf base. 2. Leaf blade size: Mature leaves 13 cm long and 3.5 cm wide. 3. Petiole length: Approximately 4.5 cm in length. 4. Leaf margin: Slightly sinuate with 3–5 pointed lobes on either side of the leaf blade. 5. Leaf texture: Slightly undulant and twisted at the tip. (i) Upper surface: Slightly pubescent with short, white trichomes evenly distributed throughout the leaf surface. (ii) Under surface: Slightly pubescent. 6. Leaf color: Green. (i) Upper surface: Near R.H.S. 147A. (ii) Under surface: Lighter than R.H.S. 147A. 7. Venation: Palmately branched with light green colored mid-vein on the upper surface. One prominent mid-vein is slightly raised on the lower surface. 8. Foliage fragrance: Characteristic Osteospermum plant fragrance, particularly notable when foliage is wet.

Flower description: Daisy type composite flower with disk and ray florets that close at night and open in the morning. The ligulate petal of the ray floret subtends the pistil. The disk florets contain male flower parts. Florets on the flower heads are imperfect with pistillate ray flowers and staminate disk flowers.

A. *Flowering habits.*—Flowering is determinate with one primary flower at the end of a long (16 cm) pedicel on open flowers. Each pedicel had approximately 5 leaflets on the proximal end of the pedicel. A secondary flower arises from the base of the primary pedicel.

B. *Natural flowering season.*—Flowering occurs primarily February through October in the northern hemisphere. Initiation occurs after a cool termperature vernalization (10°–17° C.). Floriferousness may wane during hot summer days in temperate climates. Rooted cuttings will flower in approximately 13 weeks when pinched two weeks after potting, then cultivated at 10°–12° C. for four weeks, then maintained at 18° C. for 7 weeks.

C. *Flower buds.*—Flower buds develop successively on secondary branches, reaching a size of 2 cm long and 1 cm wide prior to opening.

D. *Flowers borne.*—Singularly 5 cm above the plant canopy.

E. *Quantity of flowers.*—Secondary flowers occur progressively around the primary flower so that tight buds to mature flowers are visible at the same time.

F. *Flower head.*—1. Number of florets: 21 disk and ray florets, making up a flower disk approximately 1.1 cm in diameter. 2. Shape: Narrow linear florets with obtuse to acute tips and acute bases. Ray florets approximately 4 cm long and 0.8 cm wide. 3. Color: Ray florets are white with distinct purplish back; disk florets are blue. (i) Upper surface of ray florets: Pure white; whiter than R.H.S. 155B. (ii) Under surface of ray florets: Longitudinal stripes as dark as R.H.S. 76A and as light as R.H.S. 76D between the stripes. (iii) Disk florets: Near R.H.S. 96A. 4. Surface: (i) Upper surface of ray florets: Glabrous. (ii) Under surface of ray florets: Glabrous but pubescent near the base. 5. Flower head diameter: Up to 7.7 cm in diameter. 6. Flower fragrance: None.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and gold yellow. 4. Stigma: Bipartite. 5. Styles: Short, approximately 2 mm long and purple. 6. Ovary: Inferior to florets and green in color.

H. *Resistance.*—1. Frost: Withstands light frost. 2. Root, stem, foliage, and flower diseases: Highly resistant.

What is claimed is:

1. A new and distinct cultivar of Osteospermum plant named 'Cape Daisy Nairobi', as illustrated and described.

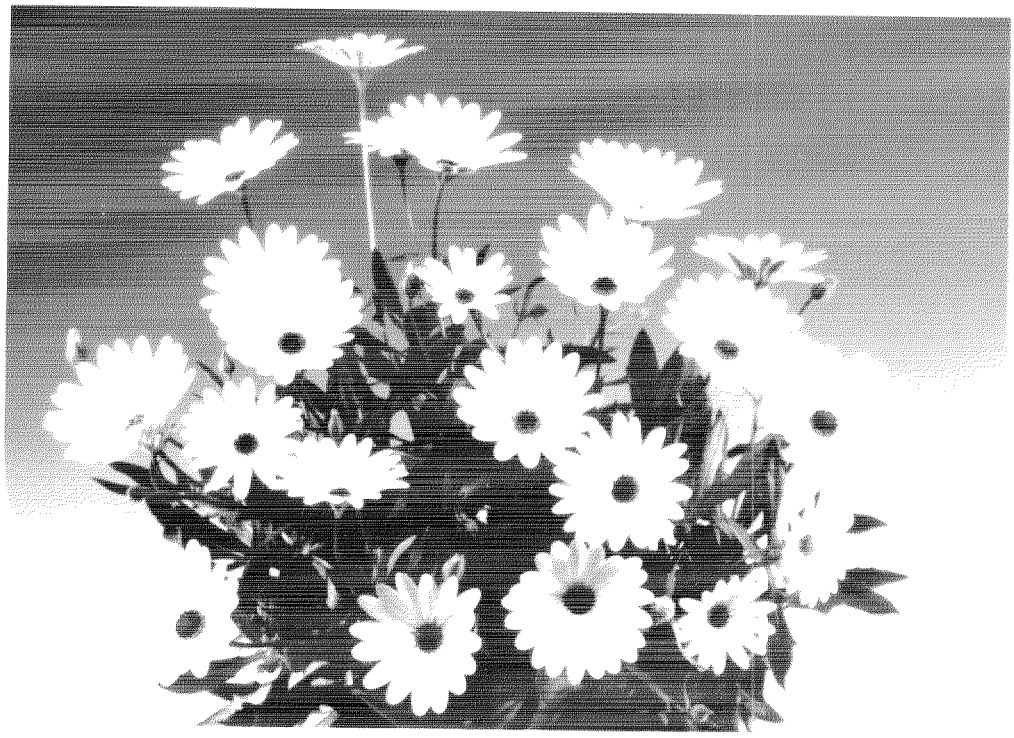

* * * * *